US012558074B2

(12) United States Patent
Johnson

(10) Patent No.: US 12,558,074 B2
(45) Date of Patent: Feb. 24, 2026

(54) SAMPLE ENCAPSULATION SYSTEM

(71) Applicant: TLC Millimeter Wave Products, Inc., Minneapolis, MN (US)

(72) Inventor: Bruce Johnson, St. Paul, MN (US)

(73) Assignee: TLC Millimeter Wave Products, Inc., Minneapolis, MN (US)

( * ) Notice: Subject to any disclaimer, the term of this patent is extended or adjusted under 35 U.S.C. 154(b) by 863 days.

(21) Appl. No.: 17/889,150

(22) Filed: Aug. 16, 2022

(65) Prior Publication Data

US 2023/0049174 A1 Feb. 16, 2023

Related U.S. Application Data

(60) Provisional application No. 63/233,729, filed on Aug. 16, 2021.

(51) Int. Cl.
A61B 10/00 (2006.01)

(52) U.S. Cl.
CPC ...... A61B 10/0096 (2013.01); A61B 10/0045 (2013.01)

(58) Field of Classification Search
None
See application file for complete search history.

(56) References Cited

U.S. PATENT DOCUMENTS 3,876,503 A * 4/1975 Mennen .................. C12Q 1/12
435/810

3,913,562 A * 10/1975 Moore ............... A61B 10/0096
435/307.1
3,915,806 A * 10/1975 Horlach ............. A61B 10/0096
435/307.1
(Continued)

FOREIGN PATENT DOCUMENTS

GB 1151771 A 5/1969
KR 20200039648 A * 4/2020 ............. B65B 9/045

OTHER PUBLICATIONS

International Search Report and Written Opinion Received for PCT/US2022/40492 on Dec. 20, 2022, 11 pgs.

*Primary Examiner* — Tanzim Imam
(74) *Attorney, Agent, or Firm* — Spencer Fane, LLP

(57) ABSTRACT

A method for sample encapsulation. A first sampling swab is provided that includes an absorbent portion and a fluid control portion that extends from the absorbent portion. The absorbent portion is proximate a proximal end of the first sampling swab. The fluid control portion is proximate a distal end of the first sampling swab. A sample is collected with the absorbent portion. At least a portion of the sample is liquid. An encapsulation material is provided that includes a first web and a second web. The first sampling swab is positioned between the first web and the second web. The first web is urged into contact with the second web proximate the absorbent portion. The urging of the first web into contact with the second web proximate the absorbent portion causes liquid to move from the absorbent portion towards the fluid control portion. The urging of the first web into contact with the second web proximate the absorbent portion is discontinued which causes the liquid to be drawn into the absorbent portion. The first web is urged into contact with the second web proximate the distal end of the first sampling swab to encapsulate the liquid in the encapsulation material.

20 Claims, 9 Drawing Sheets

(56)     References Cited

U.S. PATENT DOCUMENTS

| | | | |
|---|---|---|---|
| 4,137,194 | A | 1/1979 | Mccune |
| 4,720,017 | A * | 1/1988 | Pestes ................. B01L 3/50825 |
| | | | 206/569 |
| 6,010,462 | A * | 1/2000 | Stoermer, III ....... B65D 77/245 |
| | | | 600/572 |
| 6,207,000 | B1 | 3/2001 | Schwobel |
| 6,291,171 | B1 * | 9/2001 | Ricciardi ............... A61B 10/02 |
| | | | 206/572 |
| 6,406,602 | B1 | 6/2002 | Cahill |
| 8,796,381 | B2 | 8/2014 | Schwantes |
| 8,888,942 | B2 | 11/2014 | Dagenbach |
| 9,434,141 | B2 | 9/2016 | Dagenbach |
| 2005/0009200 | A1 * | 1/2005 | Guo ................... A61B 10/0038 |
| | | | 422/411 |
| 2008/0193727 | A1 | 8/2008 | Bernstein |
| 2010/0243169 | A1 | 9/2010 | Tucker |
| 2011/0190105 | A1 | 8/2011 | Fallon |
| 2014/0221871 | A1 * | 8/2014 | Belinson ........... A61B 10/0096 |
| | | | 435/287.1 |
| 2017/0233909 | A1 | 8/2017 | Wright |
| 2018/0311664 | A1 * | 11/2018 | Lansing ................... G01N 1/02 |

* cited by examiner

SAMPLE ENCAPSULATION SYSTEM

REFERENCE TO RELATED APPLICATION

This application claims priority to Provisional Application No. 63/233,729, filed on Aug. 16, 2021, the contents of which are incorporated herein by reference.

FIELD OF THE INVENTION

The invention relates generally to mechanical equipment. More particularly, the invention relates to a sample encapsulation system.

BACKGROUND OF THE INVENTION

Packaging or containment of a liquid sample is commonly done in industry for the packaging of ketchup and other condiments to facial products etc. In these applications, custom designed equipment creates tubular pouch forms while carefully timed control valves and filler tubes fill the pouch from a container of sample liquid before a final seal at the fill end is achieved. This is a well-known art that is extremely successful.

Lamination of documents is also a well-known art where documents or reasonably thin items can be laminated between two webs of lamination material that are subsequently heat sealed at the outer boundary or simply press sealed by nip rolls or platens in which case, the lamination material is coated with a pressure sensitive or cold seal adhesive.

Packaging of wet fabrics such as alcohol patches and wet wipes is commonly accomplished with equipment designed to feed and fold material from a single or dual web of pouch material. As the material to be packaged is from a bulk source there is no need to control for machine contamination or cross contamination between pouches.

Existing liquid packaging methods have no need to eliminate cross contamination between individual pouches or eliminate contact between packaging machinery elements and the sample fluid. Consequently, cross contamination and sample contact with the packaging equipment occurs.

Existing liquid packaging methods utilize a common bulk source so they are not suited for encapsulation of unique samples. Additionally, existing lamination systems are not designed to handle liquid samples.

There have been advances in non-contact material testing that utilize electromagnetic radiation to characterize the material and/or contaminants in the material. These techniques utilize a wide band of frequencies such as radio frequency, microwave, visible light and x-rays.

Samples to be treated can pose a risk to personnel due to their chemical or biological nature. The samples for non-contact analysis are often in liquid form or as solutes in liquid. Any sample introduced to a test system needs to be contained in a manner that eliminates contamination of the test equipment and any cross contamination to subsequent samples while maintaining compatibility to the test equipment.

There is thereby a need for systems and methods to acquire and contain a sample for non-contact analysis that concurrently reduces risk to personnel and contamination of test equipment as well as cross-contamination of subsequent samples. Additionally, the sample containment may require containment of fluids with minimal interference to the test method by containment materials used.

SUMMARY OF THE INVENTION

An embodiment of the invention is directed to a method of encapsulating a sample. A first sampling swab is provided that includes an absorbent portion and a fluid control portion that extends from the absorbent portion. The absorbent portion is proximate a proximal end of the first sampling swab. The fluid control portion is proximate a distal end of the first sampling swab. A sample is collected with the absorbent portion. At least a portion of the sample is liquid. An encapsulation material is provided that includes a first web and a second web. The first sampling swab is positioned between the first web and the second web. The first web is urged into contact with the second web proximate the absorbent portion. The urging of the first web into contact with the second web proximate the absorbent portion causes liquid to move from the absorbent portion towards the fluid control portion. The urging of the first web into contact with the second web proximate the absorbent portion is discontinued which causes the liquid to be drawn back into the absorbent portion. The first web is urged into contact with the second web proximate the distal end of the first sampling swab to secure the first web to the second web and encapsulate the liquid in the encapsulation material.

Another embodiment of the invention is directed to a sample encapsulation system that includes a sampling swab, an encapsulation material and two nip rollers. The sampling swab includes an absorbent portion and a fluid control portion. The absorbent portion is proximate a proximal end of the first sampling swab. The fluid control portion is proximate a distal end of the first sampling swab. A sample is collected in the absorbent portion. At least a portion of the sample is liquid. The encapsulation material has a first web and a second web. The two nip rollers that are rotatably mounted with respect to each other. When the absorbent portion is positioned between the first web and the second web and passed between the two nip rollers, the two nip rollers cause the liquid to move from the absorbent portion. The fluid control portion is formed with a length such that the liquid does not move beyond an end of the fluid control portion that is opposite the absorbent portion.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION OF THE INVENTION

Figure 1:
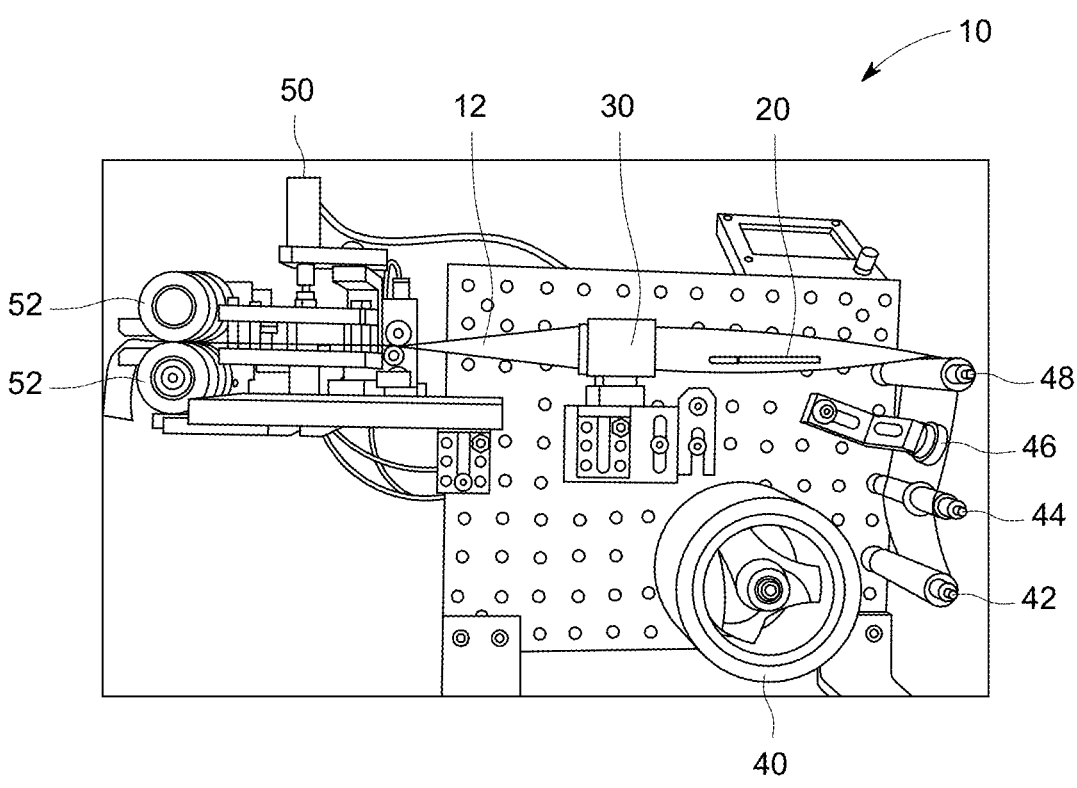
FIG. 1 is a side view of a sample encapsulation system where the sampling swab is partially positioned between an encapsulation material.
Figure 2:
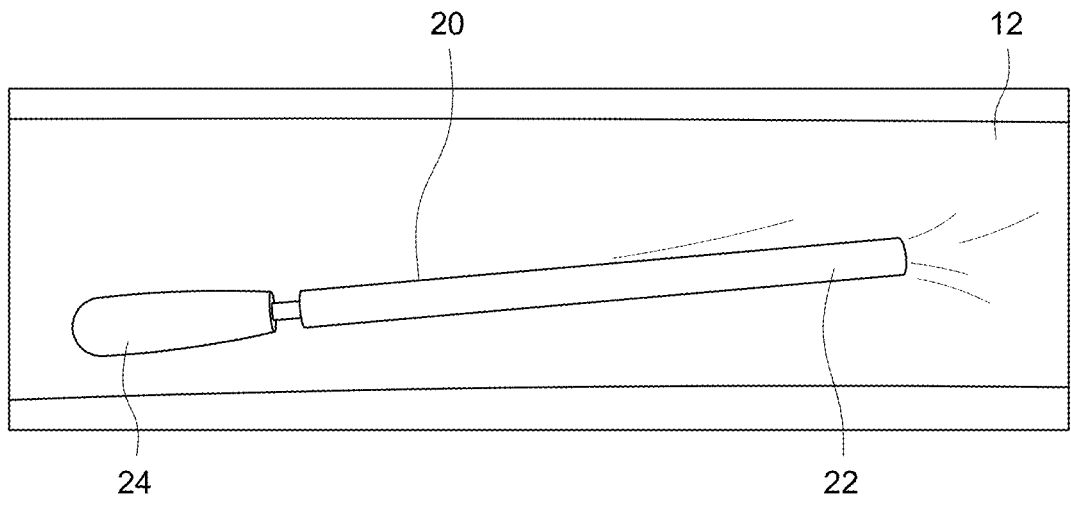
FIG. 2 is a top view of the encapsulated sampling swab.

An embodiment of the invention is directed to an automated sample encapsulation system as illustrated at 10 in FIG. 1. The automated sample encapsulation system 10 is suitable for encapsulating a sample in an encapsulating material 12 as illustrated in FIG. 2.

The automated sample encapsulation system 10 thereby prevents contact with the sample. Preventing contact with the sample prevents contamination of the sample. The invention also prevents contamination of equipment on which the sample is analyzed. The invention also protects persons who are using the automated sample encapsulation system 10.

In certain embodiments, the sample is collected from a source using a sampling swab 20 having an absorbent portion 24 at a proximal end thereof and a fluid control portion 22 at a distal end thereof. The sampling swab 20 may also include a handle extension portion (not shown) that extends from the fluid control portion 22 when required.

The configuration of the sampling swab 20 thereby enables a sample to be obtained from a variety of sources including laboratory preparations, environmental or biological (either from previously acquired samples or directly from a subject's body such as a mouth, nose, ear or rectum) while minimizing the potential that the person collecting the sample will come into contact with the sample.

The fluid control portion 22 and handle extension portion, when required, act to separate the absorbent portion 24 from personnel acquiring the sample as well as to provide fluid control during the encapsulation process. The handle extension portion, when required, may thereby be fabricated with a length based upon the location from which the sample is to be retrieved. In certain embodiments, the handle extension portion has a length of between about 2 inches and about 10 inches. In other embodiments, the handle extension portion has a length of between about 3 inches and about 6 inches.

The fluid control portion 22 may be fabricated from a variety of material using the concepts of the invention. An example of one suitable material for fabricating the fluid control portion 22 is plastic. The cross-sectional size and shape of the fluid control portion 22 are determined by the size and fluid volume capacity of the absorbent portion 24 as the critical function of the fluid control portion 22 is to insure that none of the sample fluid can be pushed beyond the end of the sampling swab 20 which could lead to cross contamination of subsequent samples. The fluid control portion 22 also permits backflow of the liquid as is described in more detail herein.

The absorbent portion 24 may be fabricated with a size based upon the volume of sample that needs to be collected. As such, the greater the size of the absorbent portion 24, the greater the volume of the sample that can be collected.

The absorbent portion 24 is sized to define the initial sample volume. Most critically it also limits the maximum amount of fluid acquired. This is critical as too large a sample volume will overcome the fluid control portion 22 of the sampling swab 24 that could lead to cross-contamination of subsequent samples.

The absorptive portion 24 also minimizes uncontrolled loss of sample liquid via splashes, dripping or aerosolizing during transfer from the sample source to the encapsulation module. Such an uncontrolled loss of sample liquid may pose a health risk to the person collecting and/or processing the sample.

The absorbent material 24 should be selected to minimize impact on the sample that is intended to be collected. As used herein, 'minimize impact' means that the absorbent material 24 does not significantly change the composition of the sample. In certain embodiments, the absorbent material 24 causes no change in the composition of the sample.

The absorbent material 24 should be selected to minimize impact on the results of the non-contact testing method that is intended to be used. As used herein, 'minimize impact' means that the absorbent material 24 does not significantly change the results of the non-contact testing that is performed on the sample. In certain embodiments, the absorbent material 24 does not have any impact on the results of the non-contact testing method that is performed on the sample.

In certain embodiments, the absorbent material 24 is expanded foam. A person of skill in the art will appreciate that it is possible to identify the particular types of expanded foam in view of the preceding comments. In other embodiments, the absorbent material 24 is a collection of fibrous elements.

In use, the absorbent portion 24 is immersed in the sample fluid. The sampling swab 20 is next placed on a web of the encapsulation material 12 as illustrated in FIG. 1 so that the absorbent portion 24 is in the direction in which the encapsulation material 12 moves during the encapsulation process.

The encapsulation material 12 should be selected to minimize impact on the sample that is intended to be collected. As used herein, 'minimize impact' means that the encapsulation material 12 does not significantly change the composition of the sample. In certain embodiments, the encapsulation material 12 causes no change in the composition of the sample.

The encapsulation material 12 should be selected to minimize impact on the results of the non-contact testing method that is intended to be used. As used herein, 'minimize impact' means that the encapsulation material 12 does not significantly change the results of the non-contact testing that is performed on the sample. In certain embodiments, the encapsulation material 12 does not have any impact on the results of the non-contact testing method that is performed on the sample.

Examples of suitable encapsulation materials 12 are webs of plastic film, paper with fluid barrier coatings, or any thin material with suitable fluid barrier properties and sufficient flexibility. The encapsulating material 12 may be of a direct seal capacity, coated with pressure sensitive adhesives, cold seal adhesives or heat seal coatings. Such coatings can in some cases also provide the fluid barrier function. These materials are specified to maximize compatibility with specific tests and sensors often without need to customize the encapsulation module.

While it is illustrated that the encapsulation material 12 is substantially transparent, it is possible for the encapsulation material to have other configurations using the concepts of this invention. For example, the encapsulation material 12 may be opaque or substantially non-transparent.

Particularly, when multiple sampling swabs 20 are encapsulated in a continuous process, precautions need to be taken to prevent cross-contamination of fluids between sampling swabs 20. Dual or folded web systems are rarely contemplated as cross-contamination is difficult to control.

Even when using many or all of the above solutions regarding sample fluid control, cross-contamination can still occur. When a web is folded to create first and second web surfaces, a fold edge is created. Due to the physical properties of most web materials and sealing methods, this fold edge cannot have a stable zero internal radius.

Consequentially, even though the radius can be less than the web thickness, a small channel, capable of allowing fluid to flow along it, can be created such that cross-contamination of samples can occur. Further, if sample fluids reach the fold edge prior to sealing, the presence of fluids can reduce or prevent stable or complete sealing at the fold edge between a first sample and a second sample.

To avoid such fluid leakage, a fold edge seal is formed proximate the fold that prevents the sample fluid from getting into the channel formed by the fold. This fold edge seal is created before the sample is introduced into the encapsulation system, thus ensuring that cross-contamination to subsequent samples does not occur along the fold edge.

Figure 4:
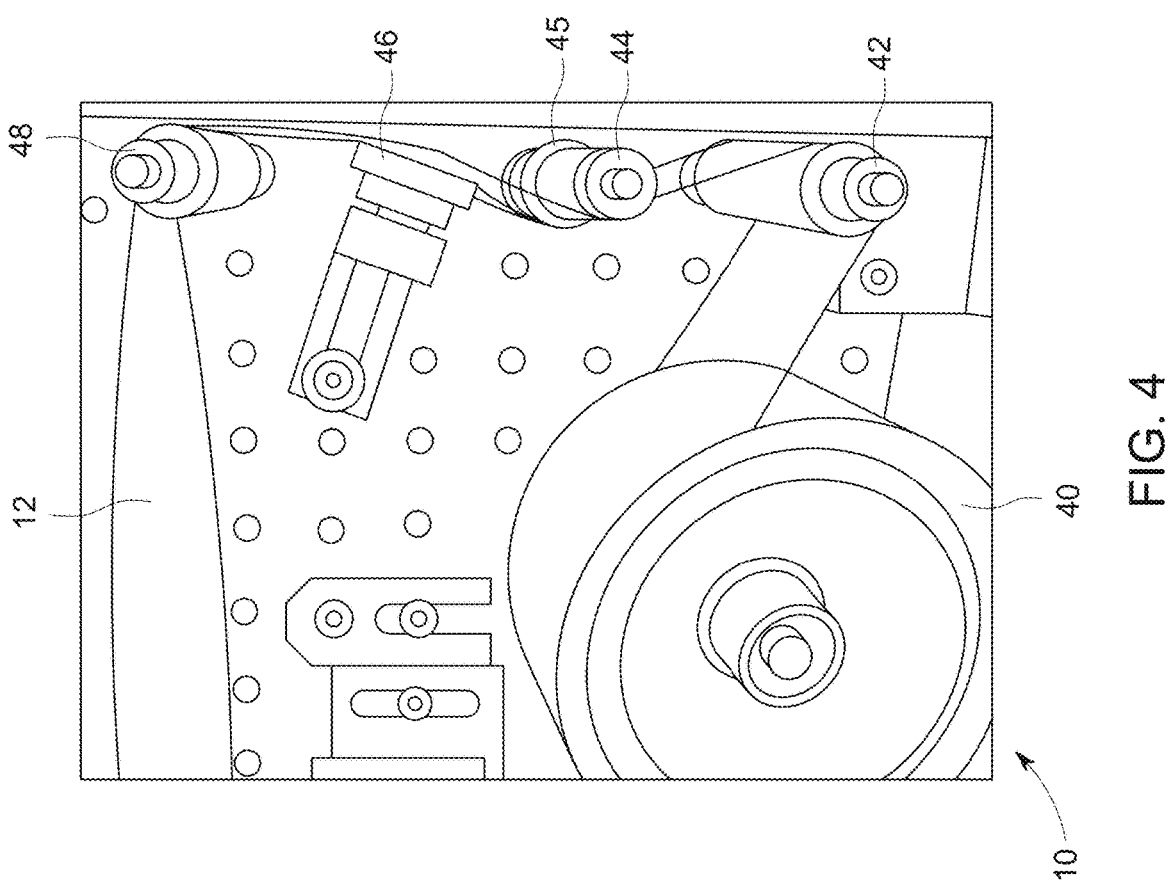
FIG. 4 is an enlarged side view of the fold edge seal portion of the sample encapsulation system.
Figure 3:
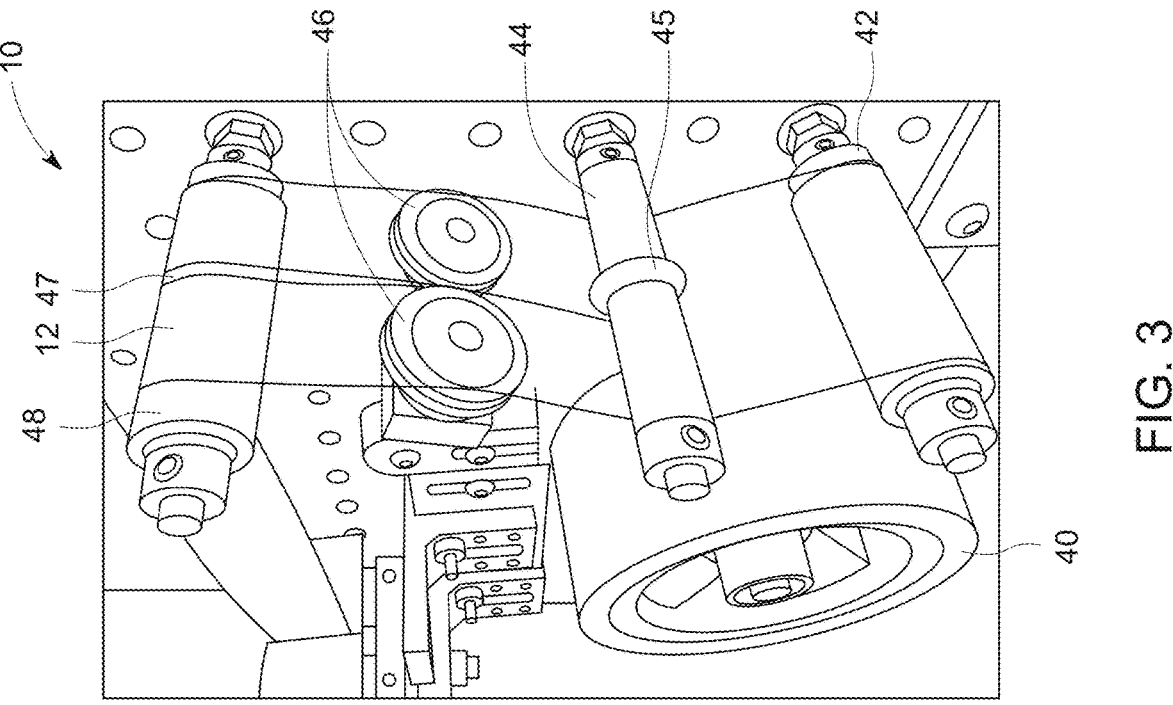
FIG. 3 is a perspective view of a fold edge seal portion of the sample encapsulation system.

FIGS. 1, 3 and 4 illustrate components of the encapsulation system 10 that create the fold edge seal. The encapsulation material 12 is stored on a roll 40 in certain embodiments. Prior to encapsulation of the sampling swab 20 in the encapsulation material 12, the encapsulation material 12 passes around a first roller 42. In certain embodiments, the first roller 42 has a width that is greater than a width of the encapsulation material 12. The first roller 42 may be rotatably mounted.

The encapsulation material 12 then passes over a fold edge roller 44. Similar to the first roller 42, the fold edge roller 44 may have a width that is greater than the width of the encapsulation material 12 and the fold edge roller 44 may be rotatably mounted.

A creasing extension 45 extends from a surface of the fold edge roller 44. In certain embodiments, the creasing extension 45 is generally intermediate opposite ends of the fold edge roller 44. A height of the creasing extension 45 is directly related to a width of a fold edge seal section 47 formed in the encapsulation material 12.

Factors that may affect the desired width of the fold edge seal section 47 include a thickness of the encapsulation material 12 and the material from which the encapsulation material 12 is fabricated. The width of the fold edge seal section 47 should be sufficiently large to reduce a potential of the two webs separating from each other after the fold edge seal section 47 is formed. On the other hand, the width of the fold edge seal section 47 should be sufficiently small to maximize the amount of the width of the encapsulation material 12 that is available for encapsulating the sampling swab 20.

In certain embodiments, the width of the fold edge seal section 47 is less than about 10 percent of the width of the encapsulation material 12. In other embodiments, the width of the fold edge seal section 47 is about 5 percent of the width of the encapsulation material 12.

After passing over the fold edge roller 44, the fold edge seal section 47 passes between two second pinch rollers 46. The second pinch rollers 46 urge the two sides of the fold edge seal section 47 together to further reduce the potential of the two sides of the fold edge seal section 47 separating from each other. The width of the second pinch rollers 46 may be selected based upon the width of the fold edge seal section 47 so that the width of the second pinch rollers 46 is approximately equal to the width of the fold edge seal section 47.

Depending on the adhesion mechanism used in the encapsulation material 12, the second pinch rollers 46 may rely solely on mechanical force. Alternatively or additionally, the second pinch rollers 46 may utilize heat to promote adhesion of the two sides of the fold edge seal section 47.

After passing between the second pinch rollers 46, the encapsulation material 12 passes around a second roller 48. In certain embodiments, the second roller 48 has a width that is greater than the width of the encapsulation material 12. The second roller 48 may be rotatably mounted.

During the encapsulating process, the encapsulating material 12 is folded to produce a first web 12a and a second web 12b. While it is illustrated that the first web 12a has a width that is similar to a width of the second web 12b, other configurations may be used.

Figure 5:
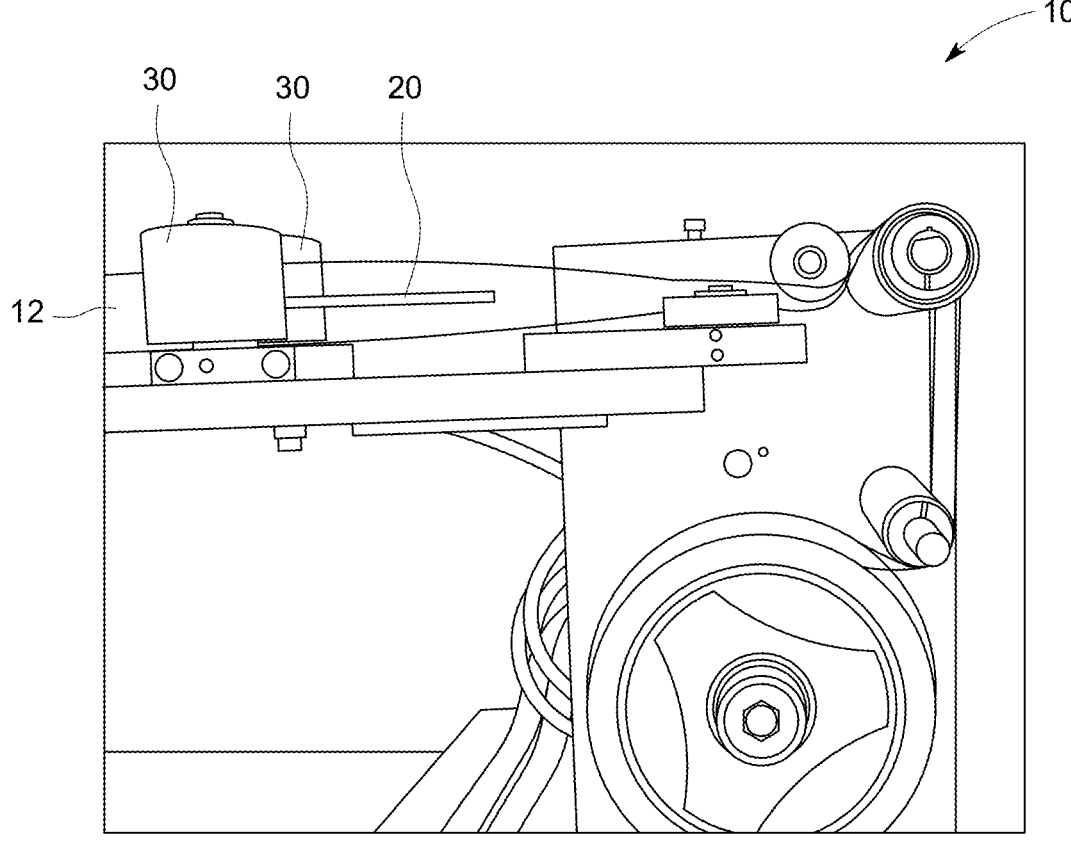
FIG. 5 is a side view of the sample encapsulation system where the sampling swab is partially between nip rolls on the sample encapsulation system.
Figure 6:
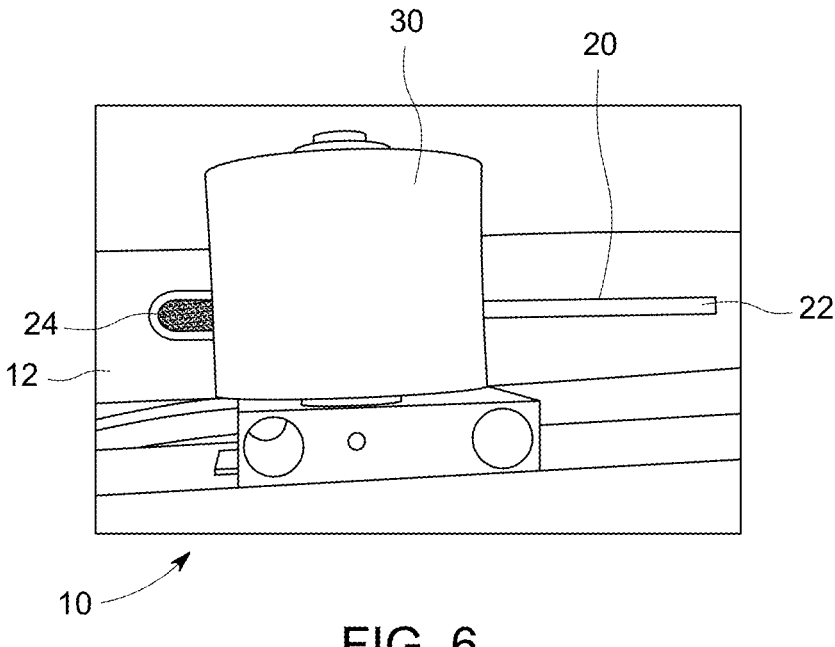
FIG. 6 is a side view of a proximal end of the sampling swab moving beyond the nip rolls.
Figure 7:
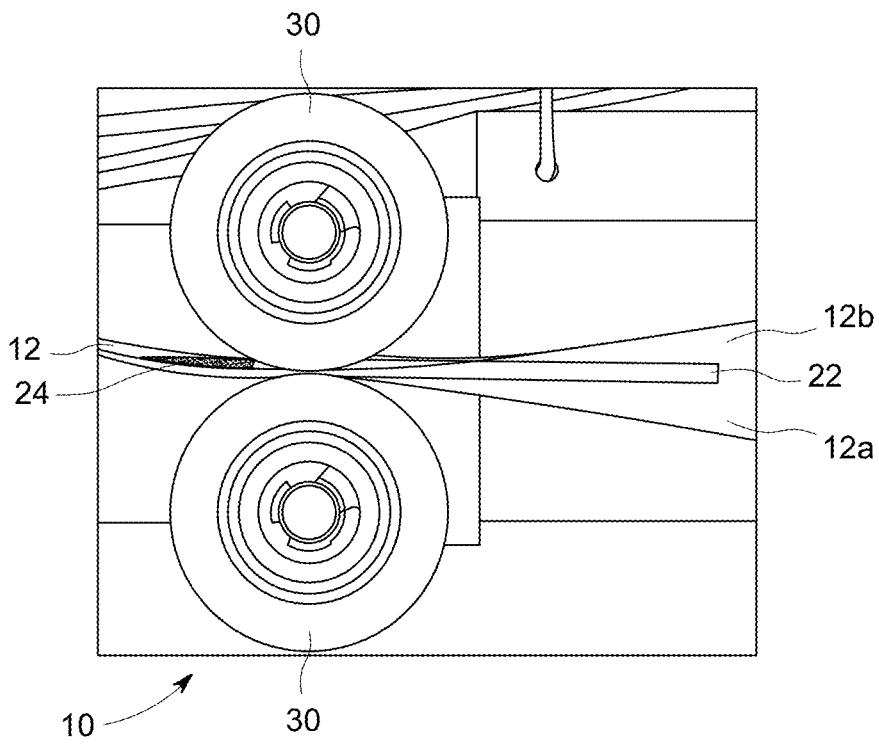
FIG. 7 is a top view of the proximal end of the sampling swab moving beyond the nip rolls.

The first web 12a and sampling swab 20 are met with the second web 12b that completes the sample encapsulation as the assembly moves through a press or pair of nip rolls 30 that join the two webs as illustrated in FIGS. 5-7. The nip rolls 30 may be a simple pressure point or one that also provides heat for heat seal applications.

In many situations, this configuration would be a simple pressure nip sufficient to seal pressure sensitive or cold seal adhesives as heat sealing can have an unwanted effect on sample chemistry. The configuration of the fluid control portion 22 allows for a unique form of fluid control during encapsulation.

When the sides of the encapsulating material 12 and sample swab 20 pass thru the nip roll 30, pressure from the nip rolls 30 causes fluid in the absorbent portion 24 to move from the absorbent portion 24 towards the fluid control portion 22, as illustrated in FIG. 5. Because the nip rolls 30 are made of a partially deformable material, such as urethane of controlled durometer, the density of and thickness or diameter of the fluid control portion 22 forms a slight depression in the nip rolls 30 that, in combination with the web material's characteristics, creates a roughly triangular shaped flow channel along the two sides of the fluid control portion 22.

This flow channel guides and controls sample fluid displacement and allows excess air to be expelled from the still open end of the assembly. This flow channel is held open while the fluid control portion 22 travels through the nip rolls 30, the absorbent portion 24, which has passed the nip roll 30, as illustrated in FIGS. 6 and 7, can now re-expand drawing the fluid sample back into the absorbent portion 24.

Figure 8:
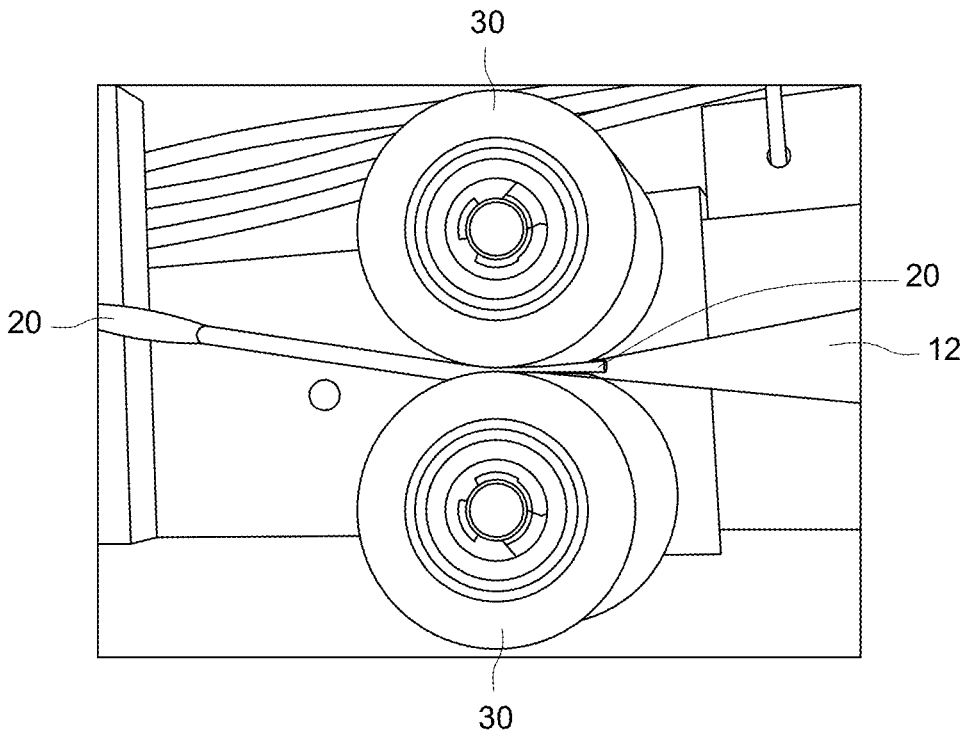
FIG. 8 is a top view showing a distal end of the sampling swab passing between the nip rolls.
Figure 9:
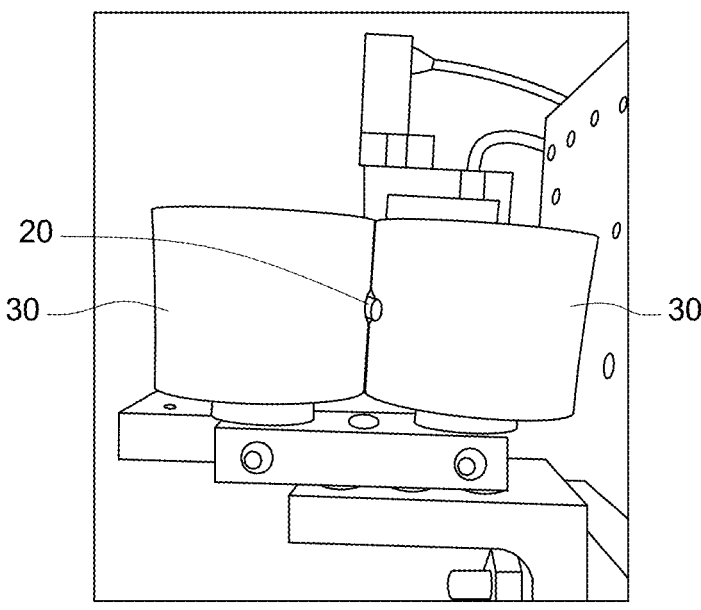
FIG. 9 is an end view of the distal end of the sampling swab passing between the nip rolls.

FIGS. 8 and 9 illustrate the distal end of the sampling swab 20 getting near the point of passing between the nip roll 30. After the absorptive portion 24 and the fluid control portion 22 have passed completely through the nip roll 30, a full seal across the encapsulation material 12 is achieved which separates each unique sample from subsequent samples. Careful design of the fluid control portion 22 insures there is no sample fluid pushed past the distal end of the sampling swab 20. This ensures full containment of the sample fluid and prevents cross-contamination of subsequent samples.

Figure 10:
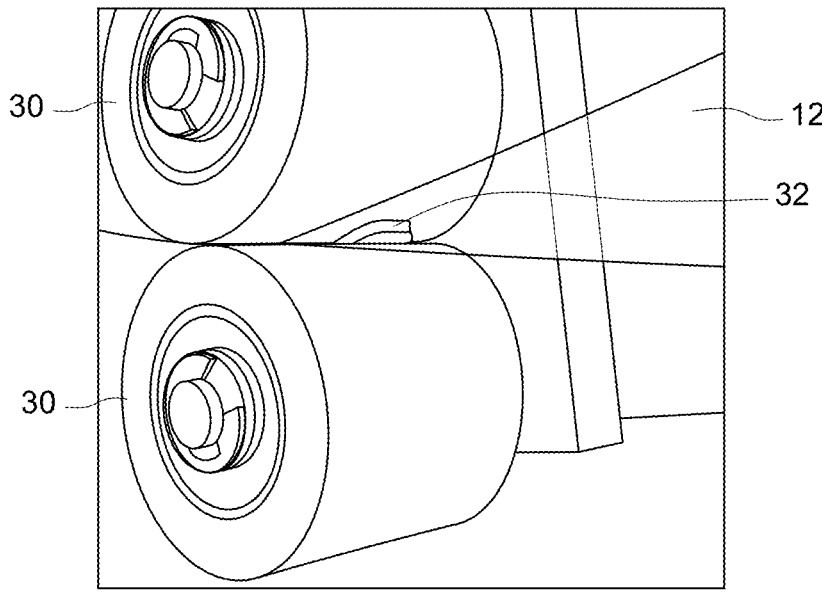
FIG. 10 is a perspective view showing flow of fluid beyond the distal end of the sampling swab after the distal end of the sampling swab has passed between the nip rolls.
Figure 11:
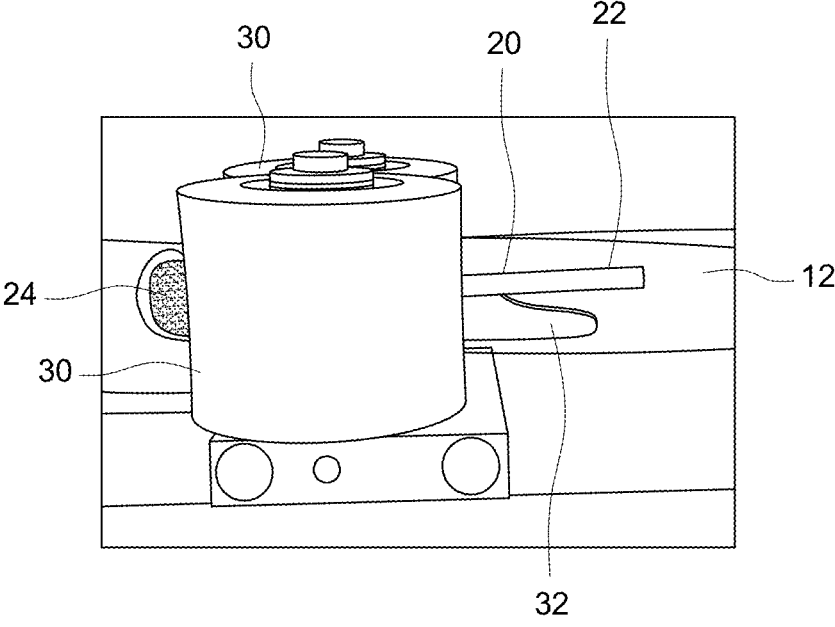
FIG. 11 is a side view show a sampling swab having too much liquid where the liquid flows from the fluid control portion.

FIG. 10 illustrates an undesired configuration where the distal end of the sampling swab 20 has passed between the nip rolls 30 and the liquid 32 is present beyond the distal end of the sampling swab 20. FIG. 11 illustrates another undesired configuration where the liquid 32 has flowed away from the fluid control portion 22. Such a configuration presents challenges for the liquid to be fully drawn back into the absorbent portion 24, which inhibits forms a reliable encapsulation.

It is desired for the fluid control portion 22 to have a length that is a short as possible because the length of the fluid control portion 22 is directly related to the length of the encapsulation material 12 that is needed to encapsulate each sampling swab 20.

Another factor that impacts the length of the fluid control portion 22 is the volume of fluid that is desired to be collected in the absorbent portion 24. In certain embodiments, the length of the fluid control portion 22 is directly related to the volume of fluid that is desired to be collected in the absorbent portion 24.

In certain embodiments, the fluid control portion 22 has a length that is longer than a diameter of the nip roll 30. Using such a configuration permits the absorbent material 24 to expand after passing between the nip rolls 30 to draw the sample fluid back into the absorbent material 24. In other embodiments, the length of the fluid control portion is longer than a radius of the nip roll 30.

The design of the fluid control portion 22 and the absorbent portion 24 replace operations and controls commonly performed by timed valves and filler tubes of pouch filling systems. This process allows a wide variety of samples to be encapsulated with a single module design utilizing smooth faced untimed nip rolls.

Figure 12:
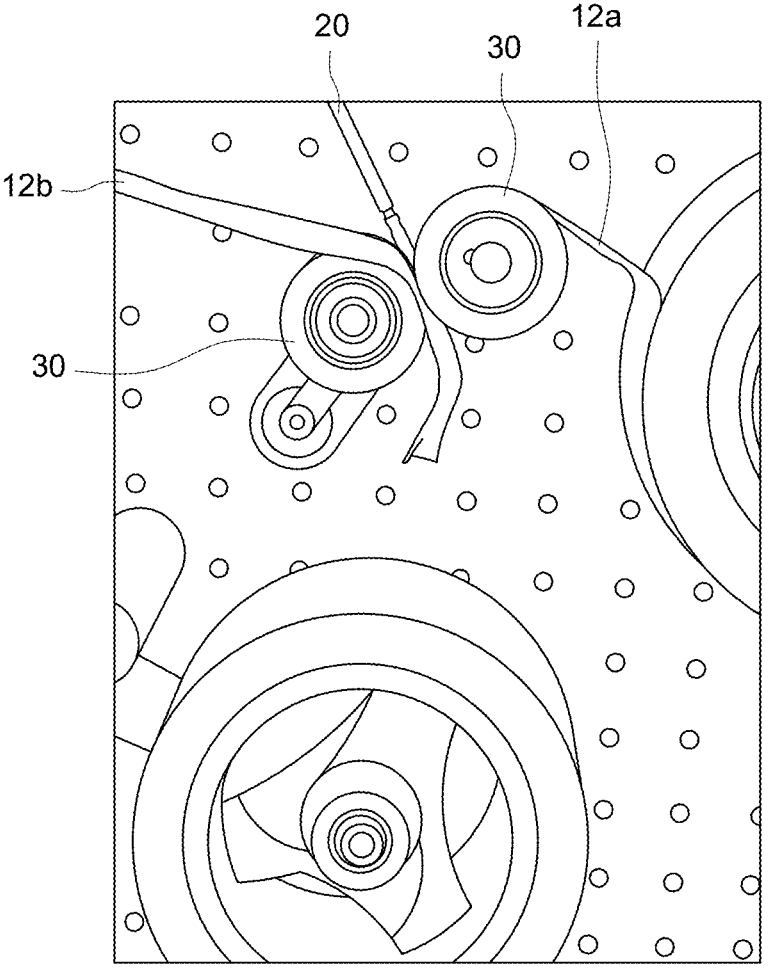
FIG. 12 is a side view of another embodiment of the sample encapsulation system where the encapsulating material is two separate pieces.
Figure 14:
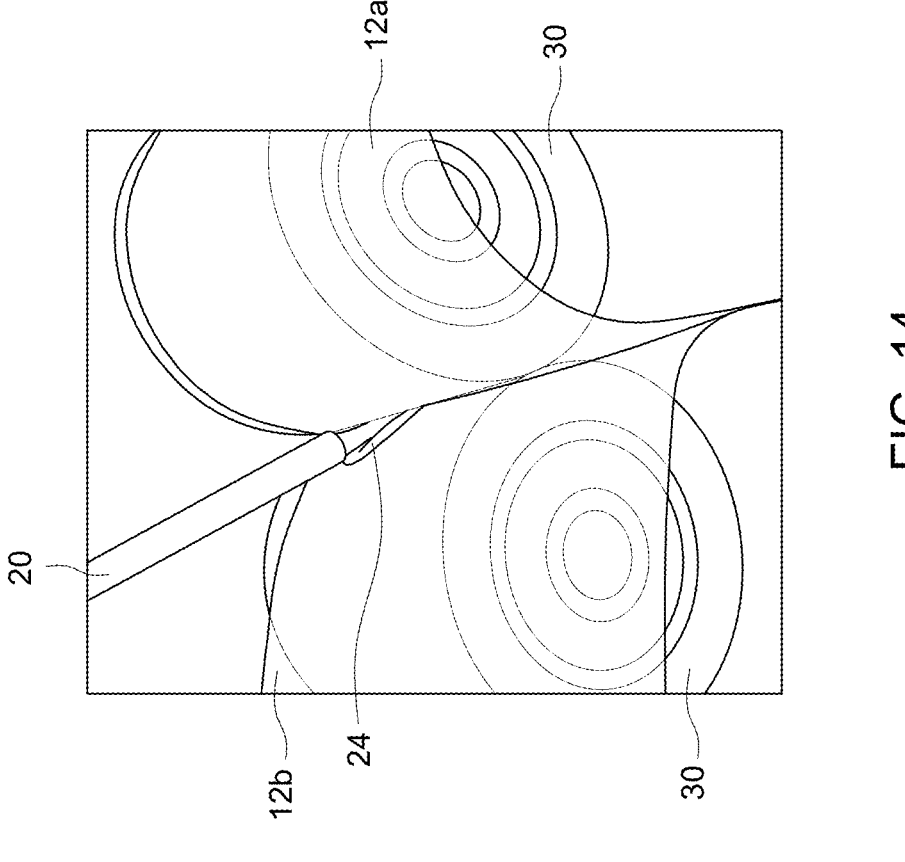
FIG. 14 is an enlarge overhead perspective view of the sampling swab further between the nip rolls in the embodiment of the sample encapsulation system in FIG. 12.
Figure 13:
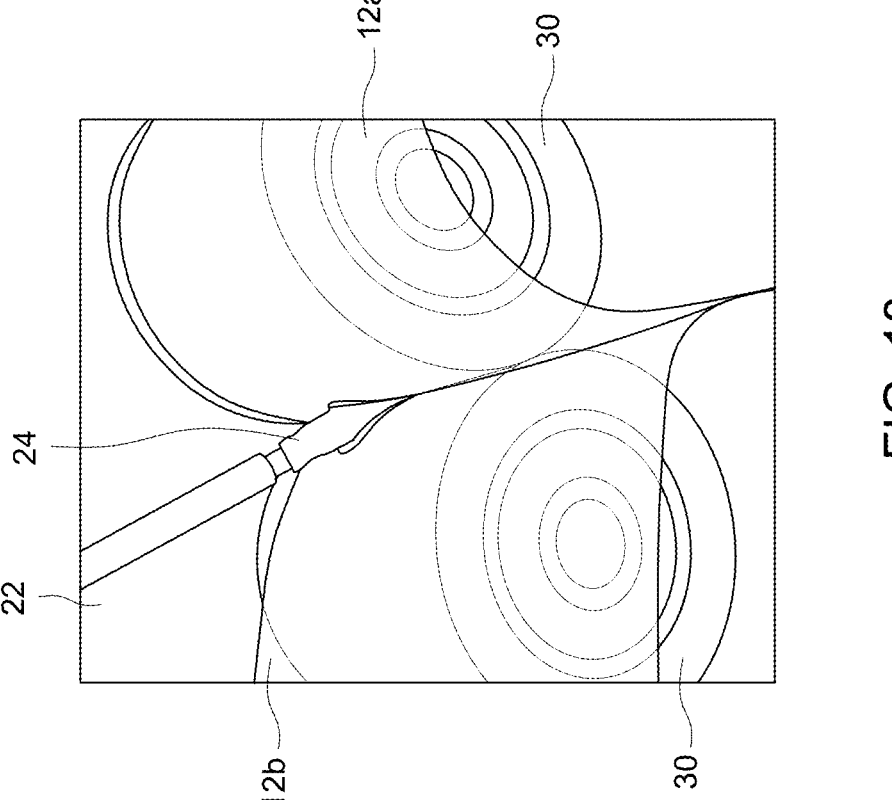
FIG. 13 is an enlarged overhead perspective view of the sampling swab partially between the nip rolls in the embodiment of the sample encapsulation system in FIG. 12.

Another embodiment of the invention, which is illustrated in FIGS. 12-14 utilizes two separate encapsulating materials 12a, 12b that are brought together at the nip rolls 30 to encapsulate the sampling swab 20. The other aspects of this embodiment are similar to the embodiment de-scribed with reference to FIGS. 1-5.

FIG. 12 shows the absorbent tip of the sampling swab 20 moving between the nip rolls 30. As the sampling swab 20 continues to move between the nip rolls 30, fluid in the absorbent material is squeezed out as illustrated in FIG. 11.

When dual webs of encapsulation material are used the nip rolls 30 can be oriented such that gravity plays a role in fluid control. Many sample fluids will not easily wet adhesive coated sur-faces or plastic films used as the encapsulating material 12. In this case the sample fluid forms a domed shape against the encapsulating web due to a large contact angle as the sampling swab enters the nip rolls.

The nip rolls 30 may be oriented such that gravity keeps the sample fluid against the nip roll 30 entry point while the absorbent portion 24 travels through the nip rolls 30 and subsequently reabsorbs the sample fluid. In cases where a large volume of sample fluid is required and the encapsulation material 12 width needs to be minimized, a timed and partial circumference groove is created in the nip roll 30 to allow a larger volume of fluid to build up at the nip roll 30 entry point.

In another embodiment, the nip rolls 30 may be grooved for a portion of their circumference that allows for a portion to have a smooth full diameter face that creates the separating seal between samples. When a grooved nip roll design is utilized, timing of the two nip rolls is required.

The sample entry port to the sample encapsulation system 10 should be designed to reduce the risk of a sampling swab contacting an unprotected surface of the sample encapsulation system 10. By utilizing encapsulation material 12 in a roll form, a fresh clean surface is provided for each new sample as the encapsulating material 12 is drawn into the nip roll zone.

Figure 15:
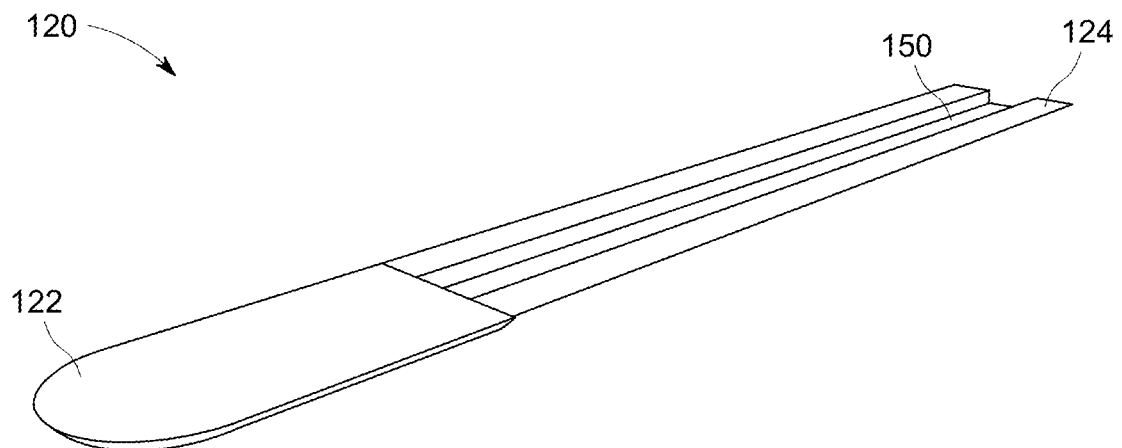
FIG. 15 is a first perspective view of a sampling swab according to another embodiment of the invention.
Figure 16:
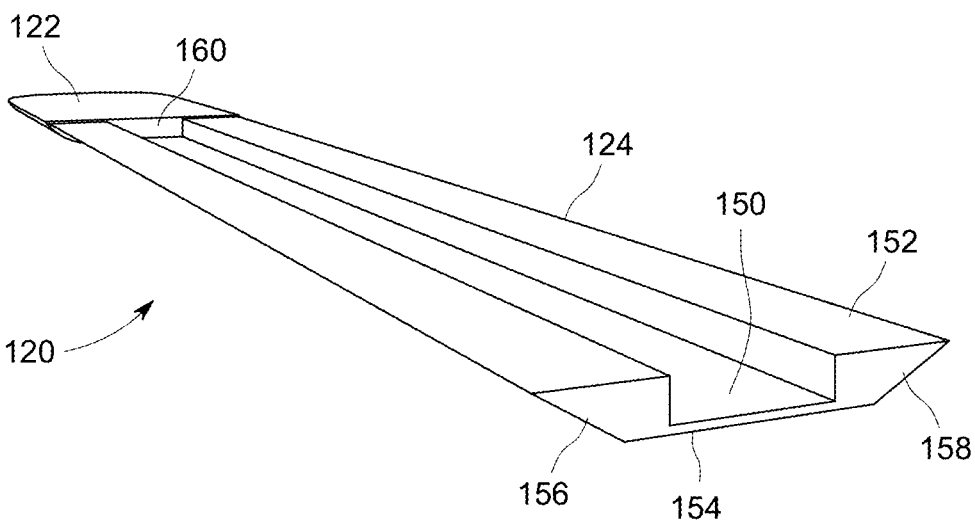
FIG. 16 is a second perspective view of the sampling swab of FIG. 15.

A sampling swab 120 according to another embodiment of the invention is illustrated in FIGS. 15 and 16. Similar to the embodiment illustrated in FIG. 2, the sampling swab 120 includes an absorbent portion 124 and a fluid control portion 122 that extends from the absorbent portion 124.

A significant difference between this embodiment of the sampling swab 120 and the embodiment of the sampling swab 20 illustrated in FIG. 2 is that the fluid control portion 122 has a channel 150 formed therein. A primary function of the channel 150 is to make it easier for the fluid to flow from the absorbent portion 124 in response to a compressive force being placed on the absorbent portion.

As such, the larger the profile of the channel 150, the higher the rate at which liquid is permitted to flow from the absorbent portion 124. One end of the channel 150 intersects the absorbent portion 124 and another end of the channel 150 extends through the end of the fluid control portion 122 that is opposite the absorbent portion 124.

While it is illustrated that the channel 150 intersects an upper surface 152 of the fluid control portion 122, it is possible for alternative configurations using the concepts of the invention. For example, the channel 150 could extend through an interior of the fluid control portion 122.

The upper surface 152, the lower surface 154, a first side surface 156 and the second side surface 158 may each be generally planar. In certain embodiments, the upper surface 152 is generally parallel to the lower surface 154. Using this configuration may enhance adhesion of the encapsulation material 12 to the fluid control portion 122 to prevent movement of the sampling swab 120 after being sealed in the encapsulation material 112.

The sampling swab 120 may include a filter material 160 that is mounted in the channel 150. In certain embodiments, the filter material may be positioned proximate the intersection of the absorbent portion 124 and the fluid control portion 122. The filter material 160 may be selected to remove certain components from the liquid that is collected in the absorbent portion 124.

In certain embodiments, the sampling swabs can be designed to include pre-analysis preparation of the fluid sample such as adding reagent chemistry or buffering compounds to the absorptive portion.

In the preceding detailed description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The preceding detailed description, therefore, is not to be taken in a limiting sense, and the scope of the present invention is defined by the appended claims.

It is contemplated that features disclosed in this application, as well as those described in the above applications incorporated by reference, can be mixed and matched to suit particular circumstances. Various other modifications and changes will be apparent to those of ordinary skill.

The invention claimed is:

1. A sample encapsulation method comprising:
   providing a first sampling swab comprising an absorbent portion and a fluid control portion that extends from the absorbent portion, wherein the absorbent portion is proximate a proximal end of the first sampling swab and wherein the fluid control portion is proximate a distal end of the first sampling swab;
   collecting a first sample with the absorbent portion, wherein at least a portion of the first sample is liquid;
   providing an encapsulation material comprising a first web and a second web;
   positioning the first sampling swab between the first web and the second web;
   urging the first web into contact with the second web proximate the absorbent portion, wherein the urging of the first web into contact with the second web proximate the absorbent portion causes the liquid to move from the absorbent portion towards the fluid control portion;
   discontinuing the urging of the first web into contact with the second web proximate the absorbent portion to cause the liquid to be drawn into the absorbent portion; and
   urging the first web into contact with the second web proximate the distal end of the first sampling swab to secure the first web to the second web and encapsulate the liquid in the encapsulation material.

2. The sample encapsulation method of claim 1, wherein prior to positioning the first sampling swab between the first web and the second web, the method further comprises forming a fold edge seal that joins together the first web and the second web.

3. The sample encapsulation method of claim 2, wherein forming the fold edge seal comprises:
   passing the first web and the second web over a fold edge roller having a creasing extension extending from a surface thereof to form a fold edge extension; and
   passing the fold edge extension between two rollers to cause the first web and the second web to join together at the fold edge extension.

4. The sample encapsulation method of claim 1, wherein the first web is urged into contact with the second web by passing the first web and the second web between two nip rollers.

5. The sample encapsulation method of claim 4, wherein the nip rollers are at least partially formed from a deformable material that deforms as the first sampling swab and the encapsulation material pass between the nip rollers.

6. The sample encapsulation method of claim 1, wherein the method further comprises selecting a length of the fluid control portion based upon a volume of the liquid that is collected in the absorbent portion so that the liquid that is caused to move from the absorbent portion does not move beyond the distal end of the first sampling swab when the first web is urged into contact with the second web proximate the distal end of the first sampling swab.

7. The sample encapsulation method of claim 1, wherein the urging of the first web into contact with the second web proximate the absorbent portion causes air in the absorbent portion to move from the absorbent portion towards the fluid control portion.

8. The sample encapsulation method of claim 1, wherein the first sampling swab further comprises a handle extension portion that extends from an end of the fluid control portion that is opposite the absorbent portion and wherein the method further comprises separating the handle extension portion from the fluid control portion prior to urging the first web into contact with the second web proximate the distal end of the first sampling swab.

9. The sample encapsulation method of claim 1, wherein the encapsulation material is provided on a roll, wherein the method further comprises encapsulating a second sampling swab after the first sampling swab is encapsulated in the encapsulation material, and wherein the sample encapsulation method prevents the first sample from coming into contact with a second sample that is associated with the second sampling swab.

10. The sample encapsulation method of claim 1, wherein at least one of the first web and the second web comprises an adhesive that causes the first web to adhere to the second web when the first web is urged into contact with the second web.

11. The sample encapsulation method of claim 1, further comprising heating at least one of the first web and the second web to cause the first web to adhere to the second web when the first web is urged into contact with the second web.

12. The sample encapsulation method of claim 1, wherein the first web is integrally formed with the second web and wherein the encapsulation material is transparent.

13. The sample encapsulation method of claim 1, wherein the first sample comprises at least one of a laboratory preparation, an environmental material and a biological material.

14. A sample encapsulation system comprising:
   a sampling swab comprising an absorbent portion and a fluid control portion, wherein the absorbent portion is proximate a proximal end of the sampling swab, wherein the fluid control portion is proximate a distal end of the sampling swab, wherein a sample is collected in the absorbent portion and wherein at least a portion of the sample is liquid;
   an encapsulation material comprising a first web and a second web; and
   two nip rollers that are rotatably mounted with respect to each other, wherein when the absorbent portion is positioned between the first web and the second web and passed between the two nip rollers, the two nip rollers cause the liquid to move from the absorbent portion, and wherein the fluid control portion is formed with a length such that the liquid does not move beyond an end of the fluid control portion that is opposite the absorbent portion.

15. The sample encapsulation system of claim 14, wherein a length of the fluid control portion is selected based upon a volume of the liquid that is collected in the absorbent portion so that the liquid that is caused to move from the absorbent portion does not move beyond the distal end of the sampling swab when the first web is urged into contact with the second web proximate the distal end of the sampling swab.

16. The sample encapsulation system of claim 14, wherein the nip rollers are at least partially formed from a deformable material that deforms as the sampling swab and the encapsulation material pass between the nip rollers.

17. The sample encapsulation system of claim 14, wherein the absorbent portion is fabricated from expanded foam, wherein the absorbent portion causes no change in a composition of the sample, wherein the encapsulation material causes no change in the composition of the sample, wherein at least one of the first web and the second web comprises an adhesive that causes the first web to adhere to the second web when the first web is urged into contact with the second web and wherein the first web is integrally formed with the second web.

18. The sample encapsulation system of claim 14, further comprising a channel in the fluid control portion, wherein the channel intersects the absorbent portion and wherein the channel extends to the distal end of the sampling swab.

19. The sample encapsulation system of claim 14, further comprising a filter proximate the absorbent portion, wherein the sample passes through the filter when moving from the absorbent portion.

20. The sample encapsulation system of claim 14, wherein the sample comprises at least one of a laboratory preparation, an environmental material and a biological material.

\* \* \* \* \*